United States Patent [19]

Yoshioka et al.

[11] Patent Number: 4,954,485
[45] Date of Patent: Sep. 4, 1990

[54] 2′,3′-DIDEOXY-4-THIO-URIDINE DERIVATIVES, PROCESS FOR THEIR PREPARATION AND ANTIVIRUS AGENTS USED THEM

[75] Inventors: Hidetoshi Yoshioka; Eiji Kojima; Shuji Ishida; Hiroyuki Yoshioka; Kunichika Murakami, all of Iwakuni, Japan

[73] Assignee: Sanyo-Kokusaku Pulp Co., Ltd., Tokyo, Japan

[21] Appl. No.: 200,903

[22] Filed: Jun. 1, 1988

[30] Foreign Application Priority Data

Oct. 20, 1987 [JP] Japan ................ 62-265083

[51] Int. Cl.$^5$ .............. A61K 31/505; A61K 31/70; C07D 239/56
[52] U.S. Cl. ......................... 514/49; 514/43; 514/885; 536/23
[58] Field of Search ............ 544/310; 536/23, 24; 514/269, 43, 49, 885, 310

[56] References Cited

U.S. PATENT DOCUMENTS 3,775,397 11/1973 Etzold et al. ............ 536/23
4,334,059  6/1982 Ogilvie ..................... 536/23

FOREIGN PATENT DOCUMENTS 272065  6/1988 European Pat. Off. ...... 536/23
1913384 6/1970 Fed. Rep. of Germany .... 536/23

OTHER PUBLICATIONS

Kulikowski et al., J. Med. Chem., vol. 22, (1979), p. 647, "Synthesis and Antiviral Activities. . . ".
Perlman et al., J. Med. Chem. vol. 28(1985) p. 741 "Nucleosides, 133, Synthesis of . . . ".
Kim et al., J. Med. Chem. vol. 30(1987) p. 862 "Potential Inti-AIDS Drugs".
Yarchoan et al., Scientific American, Oct. 1988, pp. 110–119 "AIDS Therapies".
Hobbs et al. Chem. Abst. vol. 78, 1434s, 1973 "Polynucleotides containing 2′-chloro-2′-deoxyribose".
"Potential Anti-AIDS drugs, 2′,3′-Dideoxycytidine Analogs".
Rideout et al., Chem. Abst. 107-40276d, (1987), "Therapeutic Necleosdes".
Furukawa et al., Chem. Pharm. Bull. vol. 18(1970) p. 554 "Studies of the Synthesis . . .".

Primary Examiner—Cecilia Shen
Attorney, Agent, or Firm—Oblon, Spivak, McClelland, Maier & Neustadt

[57] ABSTRACT

2′,3′-Dideoxy-4-thio-uridine derivatives represented by a following general formula

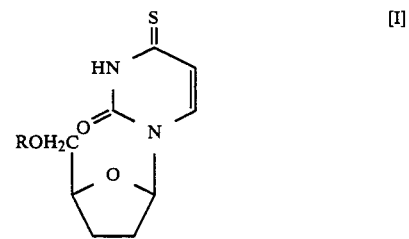

(wherein R indicates hydrogen or protecting groups such as acetyl group, benzoyl group, trityl groups, etc.), process for their preparation, antivirus agents used them as effective ingredients and therapeutic method and therapeutic drugs for virus diseases are disclosed.

12 Claims, 2 Drawing Sheets

2',3'-DIDEOXY-4-THIO-URIDINE DERIVATIVES, PROCESS FOR THEIR PREPARATION AND ANTIVIRUS AGENTS USING THEM

BACKGROUND OF THE INVENTION

The present invention relates to novel 2',3'-dideoxy-4-thiouridine derivatives and a process for their preparation.

The compounds of the invention exhibit an excellent antivirus effect and are extremely useful also, for example, as a therapeutic drug for AIDS being a virus disease.

As a result of diligent investigations of an novel compounds having antivirus effect and being low in toxicity, the inventors have found that 2',3'-dideoxy-4-thio-uridine and the derivatives thereof exhibit excellent antivirus effect and are extremely useful, for example, as a therapeutic drug for AIDS.

SUMMARY OF THE INVENTION

The invention is concerned in 2',3'-dideoxy -4-thio-uridine derivatives represented by a following general formula [I], antiAIDS virus agents having these as effective ingredients and therapeutic method and therapeutic drugs for virus diseases such as AIDS etc.

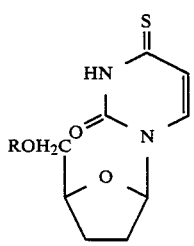

[I]

(wherein R indicates hydrogen or protecting groups such as acetyl group, benzoyl group, trityl group, etc.).

Further, the invention provides a process for the preparation of 2',3'-dideoxy-4-thio-uridine derivatives represented by a following general formula [I']

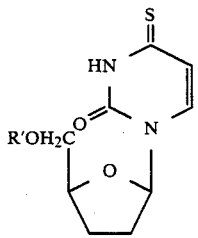

[I']

(wherein R' indicates protecting groups such as acetyl group, benzoyl group, trityl group, etc.), characterized in that, with 2',3'-dideoxy-uridine derivatives represented by a following general formula [II]

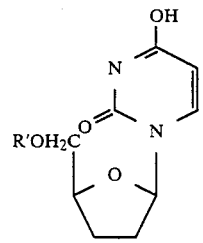

[II]

(wherein R' is same as described above), phosphorus pentasulfide is allowed to react in pyridine, and a process for the preparation of 2',3'-dideoxy-4-thio-uridine represented by a following general formula [I'']

[I'']

characterized in that 2',3'-dideoxy-4-thio-uridine derivatives represented by the following general formula [I']

[I']

(wherein R' indicates protecting groups such as acetyl group, benzoyl group, trityl group, etc.), are hydrolyzed.

DETAILED DESCRIPTION OF THE INVENTION

Figure 1:
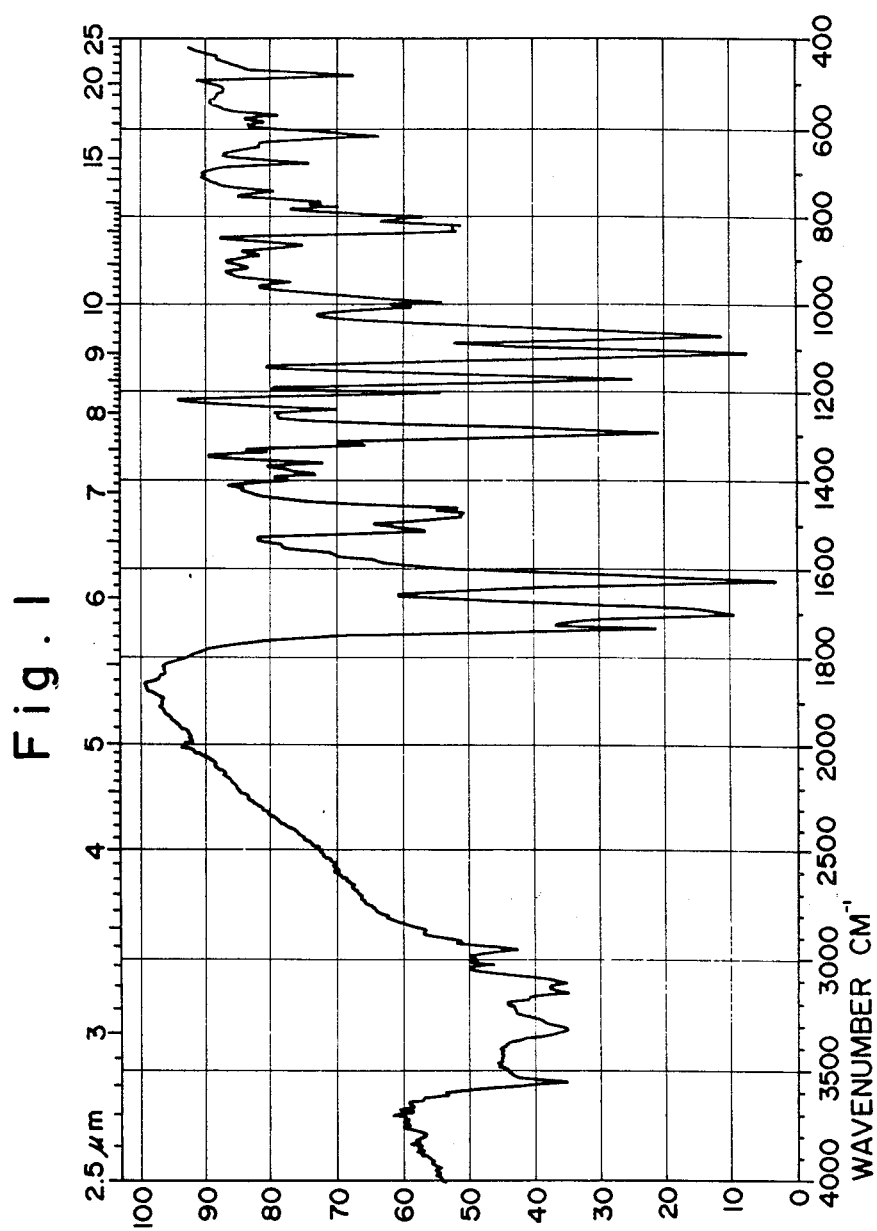
FIG. 1 shows IR spectral chart of the compound of the invention and FIG. 2 shows UV spectral chart of the compound of the invention, respectively.

The compounds of the invention can be prepared easily through a following process using 2',3'-dideoxy-uridine as a raw material.

Namely, using 2',3'-dideoxy-uridine as a raw material, the hydroxyl group on 5'-position is first protected by appropriate protecting groups such as acetyl group, benzoyl group, trityl group, etc. and then, by allowing to react with phosphorus pentasulfide in pyridine, it can be converted easily to corresponding 2',3'-dideoxy-4-thio-uridine derivatives. By eliminating the protecting groups from these derivatives according to usual method, 2',3'-dideoxy-4-thio-uridine being the compound of the invention is obtained in high yield.

When the 2',3'-dideoxy-uridine derivatives being raw materials in the invention are allowed to react with phosphorus pentasulfide in pyridine solvent, the amount of phosphorus pentasulfide is desirable to be not less than 0.5 times mol, preferably 1 to 2 times mol to 2',3'-dideoxy-uridine derivatives. In order to raise the yield of reaction further, it is preferable to add water to the reaction system and the amount of water to be added therefor is preferable to be 0.5 times mol to equivalent mol to phosphorus pentasulfide. Although the reaction proceeds without the addition of water, the reaction liquor becomes blackish brown and tarry substances are produced at this time resulting in the lowering in yield by several steps. The reaction completes by refluxing for 2 to 5 hours. After the completion of reaction, the pyridine solution is concentrated to distill off pyridine and the residue is extracted with chloroform. Thus, aimed 2',3'-dideoxy-4-thiouridine derivatives can be obtained easily in a yield of not less than 95 %. Following this, by eliminating the protecting groups with alkali or acid according to usual method, 2',3'-dideoxy-4-thio-uridine being the compound of the invention can be prepared in high yield and yet with ease.

The compound of the invention prepared in this way can be purified easily by ordinary purifying method, for example, column chromatographic method, recrystallizing method or combination of these.

Moreover, 2',3'-dideoxy-uridine or the derivatives thereof being the raw materials can be obtained easily from uridine being a constituting ingredient of ribonucleic acid by known method. For example, in the method described in Chem. Pharm. Bull., 18(3), 554–560, 1970, uridine is treated with methanesulfonyl chloride in pyridine solvent to convert to 2',3',5'-tri-O-methanesulfonyluridine and, by allowing this to react with sodium benzoate in acetamide or dimethylformamide solvent, 2,2'-anhydro-1-(5'-O-benzoyl-3'-O-mesyl-$\beta$-arabinosyl)uracil is obtained. This is allowed to react with hydrogen bromide or acetyl bromide to convert to 5'-O-benzoyl-2'-bromo-2'-deoxy-3'-O-mesyluridine and then this is treated with palladium carbon or Raney nickel catalyst in ethanol under atmosphere of hydrogen to obtain 5'-O-benzoyl-2',3'-dideoxy-uridine in a yield of about 60% (Chem. Pharm. Bull., 18(3), 554–560, 1970).

In following, an example of the invention will be shown.

(1) PREPARING EXAMPLE

Into 50 ml of pyridine were dissolved 3.16 g of 5'-benzoyl-2',3'-dideoxy-uridine and 0.22 g of distilled water. Then, after added 2.67 g of phosphorus pentasulfide at room temperature under stirring, the mixture was refluxed for 3 hours. After the completion of reaction, the solids deposited by allowing to cool were collected by filtration, which were washed with small amount of pyridine. The pyridine filtrate obtained was concentrated to dryness and the residue was extracted with chloroform to separate 3.15 g of 5'-benzoyl-2',3'-dideoxy-4-thio-uridine(yield: 95%).

Then, this was dissolved into 40 ml of 2% methanol solution of sodium methoxide and the solution was refluxed for 1 hour. After the completion of reaction, the resultant liquor was neutralized with acetic acid, concentrated and separated for purification by means of column chromatography. The crystals thus obtained were purified again through the recrystallization from methanol to obtain 1.84 g of 2',3'-dideoxy-4-thio-uridine (yield: 85%) with following physical properties.

Pale yellow needle-like crystals, Melting point: 121°-122° C.

NMR spectrum (DMSO—d6);$\delta$ 1.40-2.70 (4H, m, $C_2'$ and $C_3'$—H)

3.80-4.30 (1H, m, $C_5'$—H)

5.10 (1H, t, $C_5'$—OH, disappeared with addition of $D_2O$)

5.90 (1H, q, $C_1'$—H)

6.25 (1H, d, $C_5$—H)

7.95 (1H, d, $C_6$—H)

12.60 (1H, bs, N—H, disappeared with addition of $D_2O$).

Elemental analysis : $AsC_9H_{12}N_2SO_3$

Calculated C;47.36, H;5.30, N;12.27, S;14.05.

Observed C;47.46, H;5.33, N;12.12, S;14.08.

IR(KBr): As shown in FIG. 1.

Figure 2:
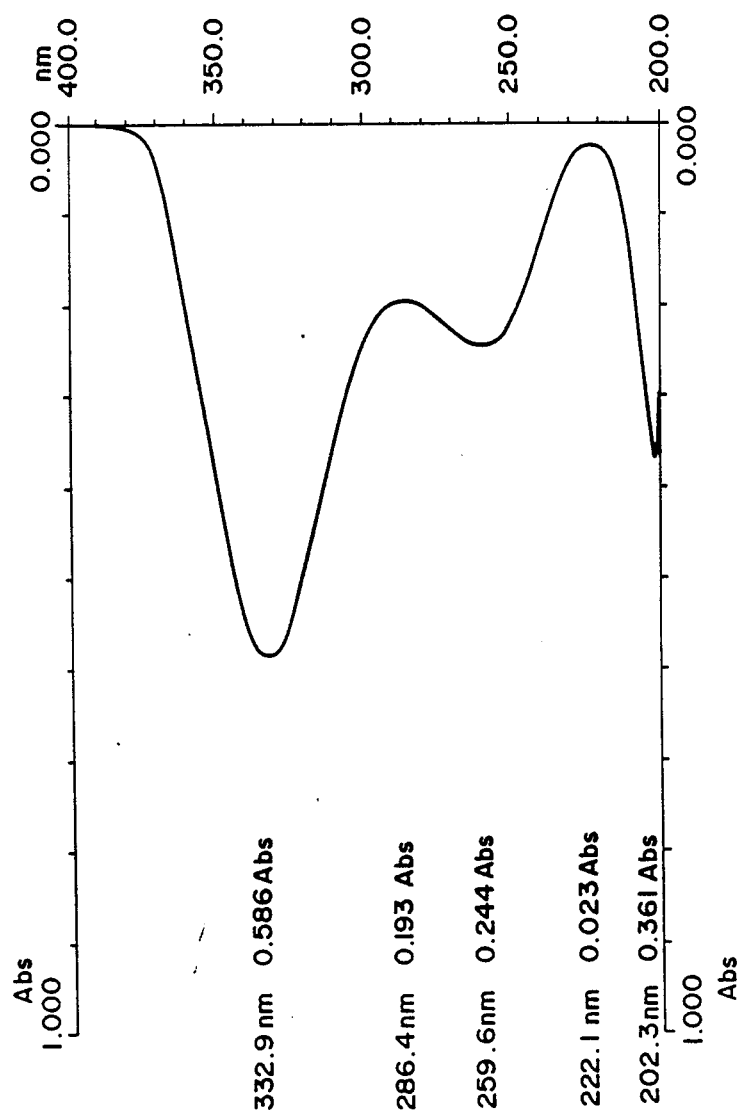

UV(EtOH): As shown in FIG. 2.

(2) ANTIVIRUS TEST

EXAMPLE 1.

The antivirus effect of the compound of general formula [II']of the invention was ascertained according to the test method by Rowe et al (J. W. Virology 1970, 42, 1136). Results are shown in Table 1.

Virus: Moloney-murine leukemia virus.

Cells: SC-1.

TABLE 1

| Antivirus effect | |
|---|---|
| Compound tested | $ED_{50}$ ($\mu M$) |
| Compound of invention | 3.7 |
| AZT | 0.02 |
| DDC | 4.0 |

(Note)
ED: Effective dose
$\mu M$: Micromol
AZT: 3'-Azido-3'-deoxy-thymidine
DDC: 2',3'-Dideoxy-cytidine

EXAMPLE 2. EFFECT ON ROUS SARCOMA VIRUS (RSV)

Employing cultured cells of the first generation (chick embryo fibroblast), RSV was infected for about 30 minutes. To this were added the samples diluted stepwise, and, after 4 to 7 days, which stage the transformation of cells due to RSV infection was inhibited at was judged under microscope.

TABLE 2

| Antivirus effect (on RSV) | |
|---|---|
| Compound tested | Concentration ($\mu g/ml$) |
| Compound of invention | 5-10 |
| DDC | 0.5-1.0 |

EXAMPLE 3.

EFFECT ON HIV (HUMAN IMMUNODEFICIENCY VIRUS)

Employing MT-4 cells, HIV was infected for 1 hour at 37° C. To this were added the samples diluted stepwise, and, after 3 days, which stage the transformation of cells due to HIV infection was inhibited at was judged under microscope.

TABLE 3

| Antivirus effect (on HIV) | |
| --- | --- |
| Compound tested | Concentration (μg/ml) |
| Compound of invention | 10 |
| DDC | 1.0 |

As shown in Table 1 through 3, the compound of the invention exhibits excellent antivirus effect similar to that of DDC. Based on this fact, it is evident that the compound of the invention is effective as a therapeutic drug for virus diseases such as AIDS etc.

As described above, in accordance with the invention, such compounds that are novel and that are excellent in the antivirus effect are provided. They are extremely effective, for example, as therapeutic drugs for virus diseases such as AIDS etc.

What is claimed is:

1. A 2′,3′-dideoxy-4-thiouridine derivative having the formula (I)

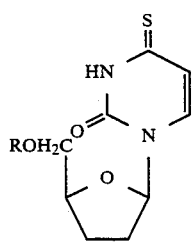

wherein R is hydrogen or a hydroxyl-protecting group.

2. The thiouridine derivative of claim 1, wherein R is hydrogen.

3. The thiouridine derivative of claim 1, wherein R is selected from the group consisting of acetyl, benzoyl and trityl groups.

4. The thiouridine derivative of claim 3, wherein R is benzoyl.

5. An antivirus pharmaceutical composition, comprising an antivirus-effective amount of a 2′,3′- dideoxy-4-thiouridine derivative having formula (I)

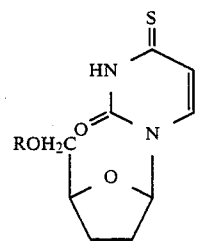

wherein R is hydrogen or a hydroxy-protecting group, and a pharmaceutically acceptable carrier, wherein said virus is selected from the group consisting of Moloney-murine leukemia virus, Rous sarcoma virus and human immunodeficiency virus.

6. The composition of claim 5, wherein R is hydrogen.

7. The composition of claim 5, wherein R is selected from the group consisting of acetyl, benzoyl and trityl groups.

8. The composition of claim 7, wherein R is benzoyl.

9. A method of treating a virus disease, comprising administering to an animal in need thereof, and antivirus-effective amount of a 2′,3′-dideoxy-4-thiouridine derivative having the formula (I):

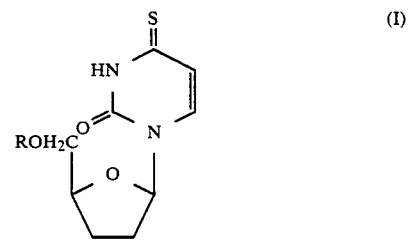

wherein R is hydrogen or a hydroxyl-protecting group, wherein said virus is selected from the group consisting of Moloney-murine leukemia virus, Rous sarcoma virus and human immunodeficiency virus.

10. The method of claim 9, wherein R is hydrogen.

11. The method of claim 9, wherein R is selected from the group consisting of acetyl, benzoyl and trityl groups.

12. The method of claim 11, wherein R is benzoyl.

* * * * *

UNITED STATES PATENT AND TRADEMARK OFFICE
CERTIFICATE OF CORRECTION

PATENT NO. : 4,954,485
DATED : September 4, 1990
INVENTOR(S) : Hidetoshi Yoshioka et al.

It is certified that error appears in the above-identified patent and that said Letters Patent is hereby corrected as shown below:

ON TITLE PAGE: Item [30]

The 2nd Priority information has been omitted, should read as follows, -- April 28, 1988 [JP] Japan  63-103892.

Signed and Sealed this

Eighteenth Day of August, 1992

*Attest:*

DOUGLAS B. COMER

*Attesting Officer*     *Acting Commissioner of Patents and Trademarks*